United States Patent [19]

Saito et al.

[11] 3,983,292
[45] Sept. 28, 1976

[54] PRESSURE SENSITIVE RECORDING PAPERS

[75] Inventors: Toranosuke Saito, Kobe; Daiichiro Tanaka, Arao, both of Japan

[73] Assignee: Sanko Chemical Company Ltd., Japan

[22] Filed: Aug. 1, 1974

[21] Appl. No.: 493,834

Related U.S. Application Data

[63] Continuation of Ser. No. 265,484, June 23, 1972, abandoned.

[30] Foreign Application Priority Data

Aug. 27, 1971  Japan............................... 46-65129
Sept. 23, 1971  Japan............................... 46-73791
Mar. 29, 1972  Japan............................... 47-30665

[52] U.S. Cl.................................. 428/306; 428/537
[51] Int. Cl.$^2$.......................................... B41M 5/12
[58] Field of Search..................... 117/36.2, 36.8; 427/151; 428/306, 537

[56] References Cited

UNITED STATES PATENTS

| | | | |
|---|---|---|---|
| 2,972,547 | 2/1961 | Tien..................... | 117/36.2 |
| 3,346,571 | 10/1967 | Spatz et al............. | 117/36.2 |
| 3,450,553 | 6/1969 | Billet et al............. | 117/36.8 |
| 3,617,335 | 11/1971 | Kimura.................. | 117/36.2 |
| 3,723,156 | 3/1973 | Brockett et al........ | 117/36.8 |
| 3,732,120 | 8/1973 | Brockett et al........ | 117/36.8 |

*Primary Examiner*—Bernard D. Pianalto
*Attorney, Agent, or Firm*—McGlew and Tuttle

[57] ABSTRACT

In a pressure sensitive recording paper which comprises in combination: a dyestuff precursor or dyestuff precursor solution and a dyestuff acceptor composition which is capable of color formation by reaction with said dyestuff precursor, the dyestuff acceptor consists essentially of a polyvalent metal salt of 3-position-substituted salicylic acid derivatives having at least 12, preferably at least 19 carbon atoms.

3 Claims, No Drawings

PRESSURE SENSITIVE RECORDING PAPERS

This is a continuation of application Ser. No. 265,484 filed June 23, 1972 now abandoned.

BACKGROUND OF THE INVENTION

The present invention relates to a pressure sensitive recording paper, particularly a novel dyestuff acceptor constituting a unit of a pressure sensitive recording paper in combination with techniques concerned with well known dyestuffs and pressure sensitive recording papers.

Pressure sensitive recording papers in the present invention are called as chemical recording papers or no carbon papers. As generally understood, the pressure sensitive recording papers mean all of such units as isolation of two or more materials being released by physical external force such as a pressure or change of a temperature, as the result those materials react each other to cause an optical change, more in detail change in absorption region of light or change in absorption intensity, and marking is effected in accordance with external forces.

Fundamentally, marking of pressure sensitive recording papers is effected by reacting a colorless or slightly colored dyestuff with a material capable of forming color of the dyestuff by a reaction therewith, namely a dyestuff acceptor, to form color. Dyestuffs in the present invention, as being understood from the following explanations, do not mean general dyestuffs in a broad sense, but mean materials which can form color by reacting with the dyestuff acceptor. The reaction means physiochemical adsorption as well as chemical reactions. Further, formation of color means such optical change as mentioned above. Heretofore, the most typical dyestuffs to be employed for pressure sensitive recording papers are Crystal violet lactone (hereinafter refered to as CVL) and benzoyl leucomethylene blue (hereinafter refered to as BLMB). Beyond them, many proton sensitive dyestuffs are known. Further, vanadium and iron containing compounds which color by forming complex compounds are known though they are essentially different from the above-mentioned dyestuffs.

Heretofore, as well known dyestuff acceptors, natural clay ores such as acid clay, bentonite, kaolinite and montmorillonite, inorganic materials such as finely powdered silicic anhydride, magnesium silicate and aluminum oxide and organic materials such as phenolic compounds, especially polyphenols, maleic resins and formaldehyde resins are known.

General pressure sensitive recording papers are composed of a microcapsule containing a dyestuff solution and a dyestuff acceptor which are coated on the surface or back surface of a paper, or a same surface, or at least one of which is made in the paper substance and the other is coated on the surface. The dyestuff solution and the dyestuff acceptor are isolated at least by shells of the microcapsules. When pressure is applied on the microcapsules in such a situation, capsules are raptured and isolation between the dyestuff solution and the dyestuff acceptor is released. As the result, the dyestuff contacts with the dyestuff acceptor and colors by a reaction, whereby marking is effected. Such mechanism or the producing technique of pressure sensitive recording papers are well known.

An object of the present invention is to provide pressure sensitive recording papers which form a bright and rich color, and can record such marking as not disappearing by influence of heat, light or water or not reducing density.

Another object of the present invention is to provide novel dyestuff acceptors which form stable and bright color by rapidly reacting with a dyestuff.

SUMMARY OF THE INVENTION

A characteristic of the present invention is a novel dyestuff acceptor which constitutes a novel unit of pressure sensitive recording papers in combination with all techniques relating to well known dyestuffs and pressure sensitive recording papers.

The dyestuff acceptor of the present invention comprises a polyvalent metal salt of aromatic carboxylic acid having at least 12 carbon atoms, represented by the general formula of

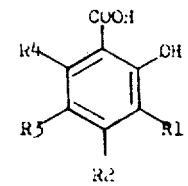

( I )

wherein $R_1$, $R_2$, $R_3$ and $R_4$ each is selected from the group consisting of hydrogen, halogen, a hydroxyl group, an alkyl group, cycloalkyl group, an aryl group, an alkyl-aryl group, an aralkyl group, an alkoxy group and an aryloxy group; two of $R_1$, $R_2$, $R_3$, and $R_4$ together may form a ring by combination with the adjacent one. Polyvalent metals represent all of other metals than lithium, sodium, potassium, rubidium, cesium and francium.

In the general formula (I), the above defined $R_1$, $R_2$, $R_3$ and $R_4$ may be the same or different. Concretely, hydrogen, chlorine, bromine, hydroxyl, methyl, ethyl, propyl, isopropyl, allyl, n-butyl, secondary butyl, t-butyl, t-amyl, cyclohexyl, phenyl, tolyl, benzyl, α-methylbenzyl, α, α-dimethylbenzyl, t-octyl, nonyl, 4-chlorophenyl, 4-bromophenyl, 4-t-butylphenyl, 4-(α, α-dimethylbenzyl) phenyl, 4-hydroxybenzyl, 3-chloro-4-hydroxybenzyl, 3-chloro-4-hydroxy-5-carboxylbenzyl, 3-carboxy-4-hydroxybenzyl, 3-t-butyl-4-hydroxy-5-carboxy benzyl, 3,5-di-t-butyl-4-hydroxybenzyl, α, α-dimethyl-4-hydroxybenzyl, α, α-dimethyl-3-carboxy-4-hydroxybenzyl, α, α-dimethyl-3-chloro-4-hydroxybenzyl, α, α-dimethyl-3-chloro-4-hydroxy-5-carboxybenzyl, α, α-dimethyl-3-t-butyl-4-hydroxybenzyl, α, α-dimethyl-3-t-butyl-4-hydroxy-5-carboxy-benzyl, α, α-dimethyl-3,5-di-t-butyl-4-hydroxy benzyl, α, α-dimethyl-3-cyclo-hexyl-4-hydroxy benzyl, α, α-dimethyl-3-cyclohexyl-4-hydroxy-5-carboxy benzyl, α, α-dimethyl-3,5-dicyclohexyl-4-hydroxy benzyl, α, α-dimethyl-3-(α', α'-dimethyl benzyl)-4-hydroxy benzyl, α, α-dimethyl-3-(α', α'-dimethyl benzyl)-4-hydroxy-5-carboxy benzyl, α, α-dimethyl-3,5-di(α', α'-dimethyl benzyl)-4-hydroxy benzyl, methoxyl, ethoxyl, butoxyl, octoxyl, phenoxyl, 4-chlorophenoxyl, 4-bromophenoxyl, 4-methyl phenoxyl, 4-t-butyl phenoxyl, 4-cyclohexyl phenoxyl, 4-t-octyl phenoxyl, 2-chlorophenoxyl, 2-cyclohexyl phenoxyl, 2-phenyl phenoxyl, 2,4-dichlorophenoxyl, 2-chloro-4-phenyl phenoxyl, 2-chloro-4-t-butyl phenoxyl, benzyloxyl, etc. are indicated. The compounds of formula (I) in which two of R1, R2, R3, and R4 together form a ring are represented by the following three general formulae;

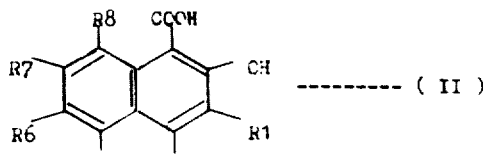

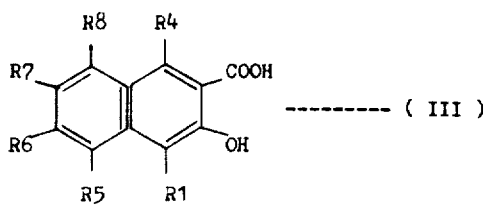

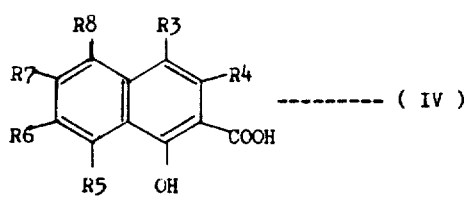

wherein R1, R2, R3, R4, R5, R6, R7 and R8 each are the same with R1~R4 in the previously defined general formula (I). In carrying out the present invention, these compounds of general formulae (II), (III) and (IV) have quite same properties with the compounds of general formula (I), and do not show different chemical properties from those of general formula (I). Therefore, it should be understood that these general formula (II), (III) and (IV) are included in formula (I).

Polyvalent metals which are concerned with the dyestuff acceptors of the present invention represent, as mentioned above, metals other than lithium, sodium, potassium, rubidium, cesium and francium. As useful metals as components for the dyestuff acceptor in the present invention, magnesium, aluminum, calcium, scandium, titanium, vanadium, chromium, manganese, iron, cobalt, nickel, copper, zinc, gallium, germanium, strontium, yttrium, zirconium, niobium, molybdenum, silver, cadmium, indium, tin, antimony, barium, tungsten, mercury, lead, bismuth, etc. are indicated. These polyvalent metals can form salts with carboxylic acid.

The most basic characteristic to be requested for a dyestuff acceptor is to form stable and rich color by rapid reaction with a dyestuff. A novel dyestuff acceptor in the present invention is most suitable for reacting rapidly with the dyestuff to form stable and rich color. Therefore, according to the present invention, a very small amount of a dyestuff acceptor or dyestuff is sufficiently used for forming a color of a desired density. Accordingly, the present invention can attain such advantages as making the weight or thickness of a recording paper smallest. Further, since the dyestuff acceptor of the present invention has quite small hardness and particle size, such disadvantages as a cutlery or types are worn out at time of cutting or printing a recording paper do not yield as generally used inorganic dyestuff acceptors. Other properties which the dyestuff acceptor should possess are sanitarily safety, economization, no influence on formation of color or no contamination by heat, light and water, no odour, or no volatility. The dyestuff acceptor in the present invention can satisfy well these properties.

Dyestuffs relating to the present invention can be divided into three types of proton sensitive dyestuffs represented by CVL, dyestuffs which color by an oxidation, such as BLMB, and dyestuffs which color by forming complexs such as vanadium or iron compounds. However, in practice, most usually used dyestuffs are proton sensitive dyestuffs represented by CVL. It is desirable that character of the dyestuff acceptor of the present invention is mainly estimated in relation with the dyestuffs of this type. It is considered that formation of color of CVL occurs by the following chemical changes.

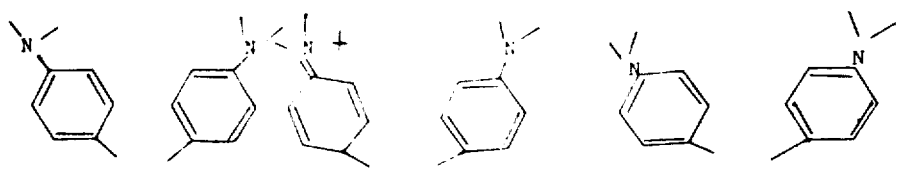

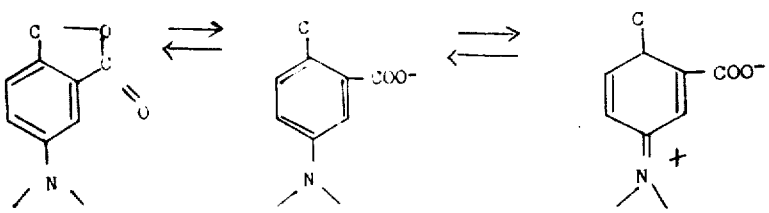

Moreover, it is considered that formation of color of BLMB occurs by the following chemical changes.

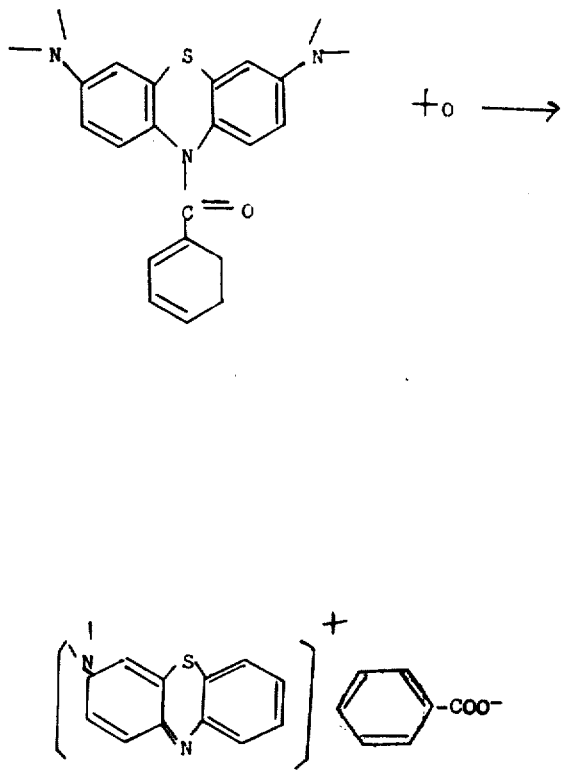

This is a reaction in which oxygen is concerned. Formation speed of BLMB is lower than the above-mentioned CVL and color of practical density can not be attained without lapse of plenty time. Therefore, in practice BLMB dyestuffs are never used singly, and it is usual that such dyestuffs are called as secondary color former and used together with proton sensitive dyestuffs such as CVL. The dyestuffs has an object of supplementing such a drawback as color formation of proton sensitive dyestuffs by the conventional dyestuff acceptor is reduced or disappears with the lapse of time or by influence of heat, light or water, Nevertheless, color formation of the proton sensitive dyestuffs by the dyestuff acceptor of the present invention is very stable and it is hardly recognized that these secondary color formers are necessary. Therefore, there is no necessity of making detailed explanations about these secondary color formers. The dyestuff acceptors must have an ability as a chelating agent (a complex forming agent) for the dyestuff which forms a complex compound and colors, such as vanadium or iron compounds. Therefore, functions of the dyestuff acceptor are essentially different from the former two, and in general aromatic polyhydroxylic compounds are used as dyestuff acceptors. Accordingly, the dyestuff acceptors which are relative with vanadium or iron compounds will be explained separately for avoiding confusion of understanding.

DETAILED DESCRIPTION

CVL is one of proton sensitive dyestuffs, in other words, electron donative dyestuffs, as mentioned above. Many reports about color formation of this kind of dyestuffs have been made and well known, but necessary matters for making the present invention understood are explained here.

CVL colors by acid. For example, proton donors such as acetic acid, propionic acid, phenol or acid clay have color forming ability. In order to make consideration easy, experiments about a uniform system are stated below.

When a phenol is added to CVL, dark blue color is formed. It means that phenol is a proton donor. When a compound including a group with a property of donating electrons such as ketone, ether, ester, nitrate, sulfon, sulfoxide, sulfide, amine, amide, nitrile, phosphoric acid ester, or phosphorous acid ester, etc. is added to the color-former solution, color disappears. The essence of this phenomenon can not be explained sufficiently but it is presumed that these compounds are combined with proton to weaken activity of proton. Relation between CVL and aliphatic acid is more complicated. When acetic acid, propionic acid, butylic acid, caproic acid or caprylic acid is added to CVL, formation of color is caused in case of acetic acid, propionic acid and butylic acid, but scarcely caused in case of caproic acid and caprylic acid. Any of aliphatic acids having more carbon atoms have no color forming ability. However, CVL colors in the case when methanol, ethanol or propanol coexists with these aliphatic acids with more carbon atoms. On the cortrary, when a comparatively low polar solvent such as benzene, toluene or xylene is added into the CVL solution which colored with acetic acid, color disappears. It is a phenomenon which occurs in common with the solution colored with aliphatic acids having many carbon atoms, alcohol and CVL. At a glance, it is considered that formation of color is relative with polarity of the solution, namely inductivity. However, since formation of color of CVL by phenol is not affected by the low polar solvent, it can not be said simply that color formation is relative with inductivity. Aliphatic acids have a carbonyl group having electron donative property like ketone and esters. It is presumed that the carbonyl group obstructs formation of color as ketone and esters. It is observed from infra-red absorption spectrum and nucleus magnetic resonance spectrum that carbonyl group of aliphatic acid forms hydrogen bond together with hydroxyl group. Moreover, it is observed, simultaneously that the degree of hydrogen bond changes according to the number of carbon atoms of the aliphatic acid, and the hydrogen bond is broken by presence of the low polar solvent or heating. It can be presumed from these observation of hydrogen bond that aliphatic acid may color CVL at time when carbonyl group of aliphatic acid forms sufficient hydrogen bond. When phenol with a comparatively similar molecular structure is compared with benzoic acid, it can be observed that phenol forms more densely color of CVL than benzoic acid. However, if methanol is present, color formed with phenol becomes pale and color formed by benzoic acid becomes dense. As the result, it is found that benzoic acid forms color of CVL more densely than phenol, when a low polor solvent is added further, therein, color almost disappears. It is known that salicylic acid has hydroxyl group at orthoposition of benzoic acid, and carbonyl group and hydroxyl group form a strong hydrogen bond in the molecule. Salicylic acid makes rich color of CVL, but is not affected by the low polar solvent. It can be understood because hydrogen bond in the molecule is quite hardly released. In practice, color reaction carried out on a recording paper occurs usually in the presence of a low polar solvent. Therefore, mechanism of color formation of carboxylic acid which does not form hydrogen bond in the molecule, as mentioned above, can not be expected as it is. Color does not disappear when alcohol is added to the solution colored by phenol or salicylic acid, but the density is reduced. From the view of this fact it is presumed that hydroxyl group with a small dissociation degree is injurious in formation of color without obstacle of coarbonyl group and alcohol of which hydrogen bond is raptured is more injurious. It is considered because of oxygen as in case of ether. As mentioned above, it can be understood that when obstacle of color formation of carbonyl group in carboxylic acid is avoided, color-forming properties of carboxylic acid by a proton sensitive dyestuff becomes greater. Polyvalent metal salts of carboxylic acid have greater color-forming properties than free acids though the system becomes non-homogeneous. This will be easily understood, considering possibility that polyvalent metals have auxiliary valencies, are co-ordinated somewhat to oxygen of carbonyl group or hydroxyl group and have similar activity to hydrogen bond.

Color forming ability of polyvalent metal salts of aromatic carboxylic acid can be considered by dividing into aromatic carboxylic acid and polyvalent metals. Generally speaking, carboxylic acid with strong acidity can make strong combination with dyestuffs, but density of color is not always straightly relative with strength of acidity. Most of polyvalent metal salts of such acids as the pK value at 25°C, being 4.6 or less, preferably 4.2 or less have a little color-forming ability. However, if carbonyl group obstructs, in such polyvalent metal salts practically sufficient density of color can not be attained.

According to the present invention, color-obstructing property of carbonyl group is avoided by formation of hydrogen bond with hydroxyl group at its ortho-position. The relation of positions of carbonyl group and hydroxyl group is shown in the general formulae (I) ~ (IV), and it is one of essential conditions of the present invention. When to the aromatic nucleus of aromatic carboxylic acid are introduced substituents, strength of acidity is affected by kind of substituents and the position thereof. Groups which make strength of acids great are groups called as negative groups. Those groups are all common to groups which obstruct formation of color, except halogen and phenyl group. Hydroxyl group has a different way of affecting strength of acids at the substituted position from that of other substituents. Dissociation constant of benzoic acid is $6.31 \times 10^{-5}$ at 25°C, that of o-oxybenzoic acid is $1.07 \times 10^{-3}$ at 19°C, that of m-oxybenzoic acid is $8.7 \times 10^{-5}$ at 19°C, and that of p-oxybenzoic acid is $3.3 \times 10^{-5}$ at 19°C. It is understood as a result of such hydrogen bond in molecules as mentioned above that strength of acid of o-oxy benzoic acid (salicylic acid) is abnormally greater than those of others.

When hydroxyl group is present at the ortho-position as aromatic carboxylic acid having relation to the present invention, strength of the acid is sufficient for formation of color, and therefore it is rather not desirable to introduce further such negative groups as obstructing formation of color. There are the following groups as groups obstructing formation of color; i.e., $-C \equiv N$, $-CO-$, $-N=$, $-NO_2$, $-SO_2-$, $-SO-$, $-S-$, $-PO=$, $-P=$, $-CS-$, $-PS=$, $-O-$ etc. The degree of obstructing formation of color of these color formation-obstructing groups is different according to the kind, and moreover the obstruction degree changes also by the molecular structure. For example, when ethyl acetate is added to CVL colored with phenol, color disappears, but even though ethyl-α-chloroacetate is added therein, color is scarcely changed. It is considered because carbonyl group of ethyl acetate obstructs strongly formation of color, but carbonyl group of ethyl α-chloroacetate loses its electron donative property by strong electron attractive property of chlorine at its α-position. Further, when anisole is added to the same color-former, color disappears, but even though 2,6-diisopropyl-4-methylanisole is added, color is hardly changed. It is understood because oxygen of ether of anisole obstructs formation of color, while same oxygen at 2,6-diisopropyl-4-methyl anisole is sterically hindered by propyl group at 2,6-position to some degree whereby connection with the outside is cut off.

Concerned with it, it is desirable that R1 in the aromatic carboxylic acid of formula (I) is halogen, an alkyl group or an aryl group. Particularly, it takes good effects in color-forming ability of acid that the group is so big that hydroxyl group at the ortho-position is sufficiently screened. The suitable groups as R1 include chlorine, methyl, ethyl, propyl, isopropyl, butyl, tertiary butyl, tertiary amyl, cyclohexyl, phenyl, benzyl, α-methyl benzyl, α, α-dimethyl benzyl, tertiary octyl, nonyl and nucleus-substituted aryl. Especially, groups having 3 or more carbon atoms have great effect of screening hydroxyl group. Considering from utility on a commercial scale, tertiary butyl, tertiary amyl, cyclohexyl, phenyl, α-methyl benzyl, α, α-dimethyl benzyl, nonyl and nucleus-substituted aryl are selected. In formula (I), hydroxyl group at ortho-position of carboxyl group plays an essential role in attaining effects of dyestuff acceptors of the present invention, as mentioned above, but its oxygen atom will have still a little color formation-obstructing ability as anisole. By many qualitative experiments, difference in color-forming ability between the case when R1 is hydrogen having no screening effect and the case when R1 is a group having a screening effect was notable observed.

The above statements are examination on color-forming ability of proton sensitive dyestuffs effected only from a chemical standpoint from the side of the dyestuff acceptor.

Progress of formation of color practically carried out on a recording paper is more complicated, and further physical properties of the dyestuff acceptor have an important influence on formation of color on the recording paper. For example, it is desirable that the dyestuff acceptor or the reaction products of the dyestuff acceptor and dyestuffs are dissolved in a solvent of the dyestuff solution to a sufficient degree for attaining dense color. In general, the dissolution is closely relative with the number of the carbon atom constituting aromatic carboxylic acid represented by formula (I).

Color-forming ability, as dyestuff acceptors, of zinc salt of salicylic acid having 7 carbon atoms, zinc salt of 3-ethyl salicylic acid having 9 carbon atoms, zinc salt of 3-tertiary butyl salicylic acid having 11 carbon atoms, zinc salt of 3-tertiary butyl-5-methyl salicylic acid having 12 carbon atoms, zinc salt of 3-phenyl salicylic acid having 13 carbon atoms, zinc salt of 3,5-ditertiary butyl salicylic acid having 15 carbon atoms, zinc salt of 3,5-dicyclohexyl salicylic acid having 19 carbon atoms, zinc salt of 3,5-di ($\alpha$, $\alpha$-dimethylbenzyl) salicylic acid having 25 carbon atoms, zinc salt of 3-{4'-($\alpha$, $\alpha$-dimethylbenzyl) phenyl}-5-($\alpha$, $\alpha$-dimethyl benzyl) salicylic acid having 31 carbon atoms, zinc salt of 2-hydroxy-1-naphthoic acid having 11 carbon atoms, and zinc salts of many other substituted salicylic acid were examined, and as the results, dyestuff acceptor consisting of aromatic carboxylic acid having less than 12 carbon atoms, could not obtain sufficient density of the formed color under the conditions employed for the recording paper. Density of the formed color increased with increase of carbon atoms in case of the dyestuff acceptor composed of aromatic carboxylic acid having 12 or more carbon atoms. It was found that aromatic carboxylic acids having 19 or more carbon atoms could attain quite great density of the formed color, which were practically especially excellent dyestuff acceptors. In case of aromatic carboxylic acids having 12 or more carbon atoms, lyophobic property is sufficiently great and water-solubility of the polyvalent metal salt becomes small. The salts are stable in the condition of water-dispersion or water-suspension, and therefore they are suitable for applying onto surfaces of papers. Polyvalent metal salts of aromatic carboxylic acid having less than 12 carbon atoms has a little water solubility, and therefore stable water dispersion system can hardly be obtained because of reciprocal action of such polyvalent metal salts with an adhesive agent or a dispersing agent. Moreover, when the recording paper is contacted with water for a long period of time, color-formation ability is remarkable lost.

Shape of a dyestuff acceptor has a great influence on color formation. It is desirable for making contact with a dyestuff solution good, that the dyestuff acceptors are fine particles having large surface dimensions per a unit weight. According to such a production process as mentioned later, the size of particles is affected by the number of carbon atoms of aromatic carboxylic acid and kinds of polyvalent metals. Aromatic carboxylic acids having 12 or more carbon atoms are suitable for producing dyestuff acceptors of fine particles.

Next, concrete examples of aromatic carboxylic acids which are useful as components of dyestuff acceptors of the present invention are indicated. They are not selected by commercial value, but selected for making understanding of idea of the present invention easy. Therefore, they do not limit the contents of the present invention. They include 5-cyclohexyl salicylic acid, 5-phenyl salicylic acid, 5-benzylsalicylic acid, 5-($\alpha$-methylbenzyl) salicylic acid, 5-($\alpha$, $\alpha$-dimethylbenzyl) salicylic acid, 5-tertiaryoctyl salicylic acid, 5-nonylsalicylic acid, 5-benzyloxy salicylic acid, 5-octoxysalicylic acid, 3-cyclo hexylsalicylic acid, 3-phenylsalicylic acid, 3-benzylsalicylic acid, 3-($\alpha$-methylbenzyl) salicylic acid, 3-nonylsalicylic acid, 3-methyl-5-tertiary butyl salicylic acid, 3-methyl-5-tertiaryamyl salicylic acid, 3-methyl-5-cyclohexylsalicylic acid, 3-methyl-5-benzylsalicylic acid, 3-methyl-5-($\alpha$-methyl benzyl) salicylic acid, 3-methyl-5-($\alpha$, $\alpha$-dimethylbenzyl) salicylic acid, 3-methyl-5-tertiaryoctyl salicylic acid, 3-methyl-5-nonylsalicylic acid, 3-tertiarybutyl-5-methylsalicylic acid, 3-tertiarybutyl-5-ethyl salicylic acid, 3,5-ditertiary butylsalicylic acid, 3-tertiary butyl-5-cyclohexylsalicylic acid, 3-tertiarybutyl-5-phenylsalicylic acid, 3-tertiarybutyl-5-benzylsalicylic acid, 3-tertiarybutyl-5-($\alpha$-methylbenzyl) salicylic acid, 3-tertiarybutyl-5-($\alpha$, $\alpha$-dimethylbenzyl) salicylic acid, 3-tertiarybutyl-5-ethoxy salicylic acid, 3-tertiarybutyl-5-benzyloxy salicylic acid, 3-tertiary amyl-5-methyl salicylic acid, 3-t-amyl-5-ethyl salicylic acid, 3, 5-ditertiary amylsalicylic acid, 3-cyclohexyl-5-methyl salicylic acid, 3-cyclohexyl-5-ethyl salicylic acid, 3-cyclohexyl-5-tertiarybutyl salicylic acid, 3-cyclohexyl-5-tertiary amyl salicylic acid, 3, 5-dicyclo hexylsalicylic acid, 3-cyclohexyl-5-phenylsalicylic acid, 3-cyclohexyl-5-benzyl salicylic acid, 3-cyclohexyl-5-($\alpha$-methylbenzyl) salicylic acid, 3-cyclohexyl-5-($\alpha$, $\alpha$-dimethylbenzyl) salicylic acid, 3-cyclohexyl-5-t-octylsalicylic acid, 3-cyclo hexyl-5-nonylsalicylic acid, 3-phenyl-5-chlorosalicylic acid, 3-phenyl-5-t-butylsalicylic acid, 3-phenyl-5-($\alpha$, $\alpha$-dimethylbenzyl) salicylic acid, 3-benzyl-5-methyl salicylic acid, 3-benzyl-5-ethyl salicylic acid, 3-benzyl-5-phenyl salicylic acid, 3, 5-dibenzylsalicylic acid, 3-($\alpha$-methylbenzyl)-5-methyl salicylic acid, 3-($\alpha$-methylbenzyl)-5-ethylsalicylic acid, 3-($\alpha$-methylbenzyl)-5-cyclohexyl salicylic acid, 3-($\alpha$-methylbenzyl)-5-phenylsalicylic acid, 3, 5-di($\alpha$-methylbenzyl) salicylic acid, 3-t-octyl-5-methylsalicylic acid, 3-t-octyl-5-ethylsalicylic acid, 3-t-octyl-5-cyclohexylsalicylic acid, 3-t-octyl-5-phenyl salicylic acid, 3, 5-di-t-octylsalicylic acid, 3-t-octyl-5-ethoxysalicylic acid, 3-($\alpha$, $\alpha$-dimethylbenzyl)-5-chlorosalicylic acid, 3-($\alpha$, $\alpha$-dimethylbenzyl)-5-methylsalicylic acid, 3-($\alpha$, $\alpha$-dimethybenzyl)5-ethylsalicylic acid, 3-($\alpha$, $\alpha$-dimethylbenzyl)-5-t-butylsalicylic acid, 3-($\alpha$, $\alpha$-dimethylbenzyl)-5-t-amyl salicylic acid, 3-($\alpha$, $\alpha$-dimethylbenzyl)-5-cyclohexyl salicylic acid, 3-($\alpha$, $\alpha$-dimethylbenzyl)-5-phenyl salicylic acid, 3-($\alpha$, $\alpha$-dimethylbenzyl)-5-{4'-($\alpha$, $\alpha$-dimethylbenzyl) phenyl}salicylic acid, 3-($\alpha$, $\alpha$-dimethylbenzyl)-5-nonylsalicylic acid, 3, 5-di($\alpha$, $\alpha$-dimethylbenzyl) salicylic acid, 3-($\alpha$, $\alpha$-dimethylbenzyl)-5-methoxy salicylic acid, 3-($\alpha$, $\alpha$-dimethylbenzyl)-5-ethoxy salicylic acid, 3-($\alpha$, $\alpha$-dimethylbenzyl)-5-benzyloxysalicylic acid, 3-(4'-t-butyl) phenyl-5-t-butylsalicylic acid, 3-(4'-t-octyl) phenyl-5-t-octylsalicylic acid, 3-{4'-($\alpha$, $\alpha$-dimethylbenzyl) phenyl}-5-($\alpha$, $\alpha$-dimethylbenzyl) salicylic acid, 3-cyclohexyl-5-hydroxysalicylic acid, 4-cyclohexyl-5-hydroxysalicylic acid, 3, 6-dicyclohexyl-5-hydroxysalicylic acid, 3, 6-dicyclohexyl-5-methoxy salicylic acid, 3, 6-dicyclohexyl-5-ethoxysalicylic acid, 3, 6-di-t-butyl-5-hydroxysalicylic acid, 3, 6-di-t-butyl-5-methoxy salicylic acid, 3, 6-di-t-butyl-5-ethoxysalicylic acid, 3-($\alpha$, $\alpha$-dimethylbenzyl)-5-hydroxysalicylic acid, 4-($\alpha$, $\alpha$-dimethylbenzyl)-5-hydroxysalicylic acid, 3, 6-di-($\alpha$, $\alpha$-dimethylbenzyl)-5-hydroxysalicylic acid, 3, 6-di($\alpha$, $\alpha$-dimethylbenzyl)-5-methoxy salicylic acid, 3, 6-di($\alpha$, $\alpha$-dimethylbenzyl)-5-ethoxysalicylic acid, 4-hydroxy-5-t-octyl salicylic acid, 4-hydroxy-5-($\alpha$, $\alpha$-dimethylbenzyl) salicylic acid, 3, 5-di-t-butyl-6 hydroxy salicylic acid, 3, 5-di-($\alpha$, $\alpha$-dimethylbenzyl)-6-hydroxy salicylic acid, 5-(3'-carboxy-4'-hydroxybenzyl) salicylic acid (methylene-bis-salicylic acid), 5-(3'-carboxy-4'-hydroxy-5'-t-butyl benzyl)-3-t-butylsalicylic acid, 5-($\alpha$, $\alpha$-dimethyl-3'-carboxy-4'-hydroxy-5'-t-butylbenzyl)-3-t-butylsalicylic acid, 5-($\alpha$, $\alpha$-dimethyl-3'-t-butylbenzyl)-3-t-butylsalicylic acid, 5-{$\alpha$, $\alpha$-dimethyl-3'-carboxy-4'-hydroxy-5'-($\alpha$, $\alpha$-dimethylbenzyl) benzyl}-3-

(α, α-dimethyl benzyl) salicylic acid, 5-{α, α-dimethyl-3'-(α, α-dimethylbenzyl)-4'-hydroxy benzyl}-3-(α, α-dimethylbenzyl) salicylic acid, 1-hydroxy-2-carboxy-4, 7-di-t-butyl naphthalene, 1-hydroxy-2-carboxy-7-(α, α-dimethylbenzyl) naphthalene, 1-carboxyl-2-hydroxy-3, 6, 8-tri-t-butyl naphthalene, 1-carboxy-2-hydroxy-6-(α, α-dimethylbenzyl) naphthalene, 1-carboxy-2-hydroxy-3, 6-di (α, α-dimethyl benzyl) naphthalene, 2-hydroxy-3-carboxy-6, 8-ditertiary butyl naphthalene, 2-hydroxy-3-carboxy-6-(α, α-dimethylbenzyl) naphthalene, formaldehyde condensate of hydroxyl naphthoic acids or formaldehyde cocondensate of salicylic acid and phenols.

All of the above-mentioned aromatic carboxylic acids have hydroxyl group at ortho-position to carboxylic group, and can form salts with polyvalent metals. In accordance with ratio of carboxylic acids to metals, polyvalent metal salts of aromatic carboxylic acid may contain basic salts, and neutral salts, and acid salts in case of polycarboxylic acids. Polyvalent metal salts of aromatic carboxylic acids concerned with the dyestuff acceptors of the present invention may be any of these salts. Many of the above-mentioned aromatic carboxylic acids are novel compounds, of which producing methods are similar to the methods for producing salicylic acid, and these compounds are synthesized by substituted phenol and carbon dioxide gases. Substituted phenols are obtained by alkylation of phenols. As phenols inducing aromatic carboxylic acids cited in the above-mentioned concrete example, there are indicated phenol, o-cresol, p-cresol, o-ethylphenol, p-ethylphenol, o-phenylphenol, p-phenylphenol, hydroquinone, p-methoxyphenol, p-ethoxyphenol, p-benzyloxyphenol, p-octoxyphenol, p-chlorophenol, resorcinol, bisphenol A, α-naphthol and β-naphthol. As alkylating agents, isobutylene, isopentene, cyclohexene, cyclohexyl chloride, benzyl chloride, styrene, α-methylstyrene, isooctene, isononene, formaldehyde etc. are indicated. Addition or condensation of alkylating agents to phenols is carried out in the presence of a so-called Friedel-Craft catalyst such as sulfuric acid, hydrogen fluoride, boron trifluoride, aluminum chloride, zinc chloride, ferric chloride, or stannic chloride. All of substituted phenols inducing the above-indicated aromatic carboxylic acids can be synthesized by said method. Substituted phenols are converted into sodium salts of substituted phenols by caustic sodium or metallic sodium, and the thus obtained sodium salts of substituted phenols are dehydrated completely treated with carbon dioxide gases. At that time, if water or free caustic sodium is present, yields of aromatic carboxylic acids become remarkable reduced. Carbon dioxide gases are reacted with substituted phenols under an elevated pressure. Sodium salts of substituted phenol can be reacted with carbon dioxide gases in form of powder, medium suspension of powder or solution. The reaction products contain sodium salts of aromatic carboxylic acids. Isolation as aromatic carboxylic acids can be effected for employing for the object of the dyestuff acceptor of the present invention, but purification of sodium salts may be carried out as they are. Aromatic carboxylic acids can be condensed further with formaldehyde. At that time, phenols may be present. All of aromatic carboxylic acids indicated as concrete examples can be produced by the above mentioned method.

It is right that polyvalent metals are selected depending on the colorforming abilities in relation with aromatic carboxylic acids, but many of the polyvalent metals are restricted from the point of sanitarily safety, economy, and coloring properties of metal ions. As desirable polyvalent metals, magnesium, aluminum, calcium, titanium, chromium, manganese, iron, cobalt, nickel, copper, zinc, zirconium, molybdenum, tin, antimony, lead and bismuth are indicated. Further, most suitable metals for the practical use of them are magnesium, aluminum, calcium, titanium, manganese, zinc and lead.

Two or more kinds of aromatic carboxylic acids may be mixed to feed for the object of the present invention. In many cases, when two or more kinds of polyvalent metals are mixed to use, particularly good results are attained.

One of practical characteristics of the dyestuff acceptor of the present invention is that stable reaction products with dyestuffs are formed. Accordingly, marking of pressure sensitive recording papers of the present invention not only can be kept for a long period of time, but also disappers or fades to a minimum degree even though they are exposed to heat, light, water or atmosphere of other chemical materials. As mentioned above, when excellent characteristics of dyestuff acceptors are utilized practically on pressure sensitive recording papers, the process of application thereof has a great influence on effects as dyestuff acceptors. Therefore, the method for producing polyvalent metal salts of aromatic carboxylic acid and the application thereof can be said as most important processes in the present invention. The fact will be explained hereinafter.

In many cases, polyvalent metal salts of aromatic carboxylic acids are obtained in form of fine powder. The physical form thereof is suitable for using as dyestuff acceptors for pressure sensitive recording papers. There are some processes for producing polyvalent metals of aromatic carboxylic acids. Polyvalent metal salts of aromatic carboxylic acids can be produced by mixing and reacting aromatic carboxylic acids with oxides, hydroxides, carbonates, silicates, borates, or sulfides of polyvalent metals. At that time, water or an organic solvent is used as a medium. Materials which are not homogeneous in the medium are mechanically mixed or crushed to make the reaction between them smooth. For example, when 3-phenyl salicylic acid and zinc oxide powder are crushed in a ball mill in form of an aqueous suspension the end compositions containing zinc salts of aromatic carboxylic acids are obtained. In that case, it is more effective that a small amount of ammonia and a surface active agent are present. In the same manner, the end compositions are obtained from 2-hydroxy-3-carboxy-6-(α, α-dimethylbenzyl) naphthalene and fine powder of aluminum silicate. Suitable polyvalent metal-containing materials for producing polyvalent metal salts of aromatic carboxylic acids by such a method as mentioned above include magnesium hydroxide, aluminum hydroxide, calcium oxide, titanium oxide, zinc oxide, antimony oxide, magnesium silicate, aluminum silicate, calcium silicate, zinc silicate, magnesium carbonate, calcium carbonate, zinc carbonate, barium carbonate, zinc sulfide and other mineral materials containing polyvalent metals. Generally, polyvalent metals salts of aromatic carboxylic acids prepared by the above-mentioned process contain excess amount of aromatic carboxylic acids, polyvalent metal-containing inorganic materials, or both of them, but in any cases, effects as the dyestuff acceptors of the present invention are not spoiled.

Among methods for producing polyvalent metal salts of aromatic carboxylic acids a method composed of a double decomposition is one which can be utilized simply. It is most suitable for double decomposition to use water as a medium. Most of alkali metal salts, ammonium salts or amine salts of aromatic carboxylic acids are soluble in water. When an aqueous solution of polyvalent metal salts is added into the aqueous solution of these water-soluble salts a double decomposition occurs. It is desirable that polyvalent metal salts of aromatic carboxylic acids formed by the double decomposition are practically insoluble into water. Polyvalent metal salts of aromatic carboxylic acids may be separated from a water-soluble salts by-produced at time of the double decomposition by washing with water, ion exchange or electrodialysis, but utilization of polyvalent metal salts of aromatic carboxylic acids containing water-soluble salts is possible as they are, as dyestuff acceptors. It is usual that polyvalent metal salts of aromatic carboxylic acids which are insoluble in water are obtained in form of a suspension or a dispersion in water by double decomposition. At that time, size or shape of the particles have an influence on effects as dyestuff acceptors. It is necessary for making the size or shape of particles suitable, to control carefully various conditions such as concentrations of two aqueous solutions in double decomposition, temperature, mixing speed, stirring speed or presence of a surface active agent. When too big particles, alone, are obtained in double decomposition, these particles are mechanically crushed to feed for the object as dyestuff acceptors. Generally, particles having a diameter of $0.1\mu \sim 5\mu$ can attain better effects as dyestuff acceptors. As desirable water-soluble polyvalent metal salts, there are shown haloid salts, nitrate, sulfonate, acetate or formate.

Generally, film-forming materials with medium-dispersibility or medium-solubility are added into polyvalent metal salts of aromatic carboxylic acids having medium-dispersibility or medium-solubility. The film-forming materials fix dyestuff acceptors on a substrate such as papers to prevent isolation of dyestuff acceptors. As film forming materials, there are indicated starch, gelatine, gum arabic, polyvinyl alcohol, polyacrylamide, acrylamide-methylol acrylamide copolymer, acrylamide-acrylonitrile copolymer, acrylamide-acrylester copolymer, methyl cellulose, hydroxy ethyl cellulose, polyethylene glycol, melamine resins, urea resins, sodium polyacrylate, sodium acrylate-acrylicester copolymer, carboxy methyl cellulose, carboxy ethyl cellulose, natural rubber, synthetic rubber, polyacrylic acid ester, polymethacrylic acid ester, polyvinyl acetate, vinyl acetate-ethylene copolymer, polystyrene, polyisobutylene, vinyl chloride copolymer, ethyl cellulose, nitrocellulose, cellulose acetate, phenol resins, butyral resins, petroleum resins or alkyd resins. These can be classified into three types of water-soluble, water-dispersible, or organic solvent-soluble. The water-soluble film-forming materials are divided further into non-ionic and ionic types.

These film-forming materials, particularly water-soluble film-forming materials can be added with chemical linking agents for forming water-insoluble film by the reaction. Water-insoluble film-forming materials can be dissolved in an organic solvent for their use, but they are used generally in the condition of suspension, emulsion, or dispersion in water. Anionic film-forming materials exchange their ions with polyvalent metal salts of aromatic carboxylic acids, and are gelatinized in a medium or injure effects as dyestuff acceptors in some cases. Therefore, their utilization must be well taken care of. A surface active agent is added, if necessary, for making dispersibilities of dyestuff acceptors and film-forming materials in the medium stable. Nonionic or anionic surface active agents are used. Since these secondary additives are harmful to color forming-ability of the dyestuff acceptors, it is desirable to suppress the harm to a minimum degree by examining sufficiently kind and amount of the additive.

When dyestuff acceptors with a low melting point are coated on the surface of papers and dried by heating, the dyestuff acceptors are molten to lose their shape, and permeate into paper substances, or porosity of the surface is often failed because the surface is molten and adhered. Not to fail porosity of the surface by heating, fine powder of a carrier or a support with a high melting point is added to the dyestuff acceptor with a low melting point. Moreover, in some case, the dyestuff acceptors are fine particles in form of supercooled glass conditions, though they have a high melting point in practice. It is necessary to treat in the same manner of treatment, because they are softened in some cases by heating. As fine powder with a high melting point, water-insoluble inorganic materials are desirable, and silicic anhydride, aluminum silicate, magnesium silicate, zinc silicate, aluminum borate, zinc borate, zinc oxide, magnesium carbonate, calcium carbonate, zinc carbonate and other mineral materials in form of fine powder are suitable.

The compositions containing dyestuff acceptors prepared by the above-mentioned means are applied to the surface of a support such as paper and dyestuff acceptors can be distributed uniformly over the surface. It is desirable in general that water is the medium for the composition, but drying speed of the medium or consistency of the compositions become problems in some cases according to an coating means. Therefore, an organic solvent is used.

Further, the above-mentioned double decomposition can be carried out on a carrier such as the surface of a paper. An aqueous solution of alkali metal salts or ammonium salts of aromatic carboxylic acids is applied over the surface of a paper and successively an aqueous solution of polyvalent metal salts is applied, when double decomposition occurs on the surface of the paper and dyestuff acceptors are formed. Moreover, double decomposition is caused in a suspension of pulp and polyvalent metal salts of aromatic carboxylic acids can be deposited on the surface of pulp fibers. When papers are made of this pulp, papers in which dyestuff acceptors are uniformly distributed can be obtained.

Two or more different kinds of dyestuff acceptors can be mixed to use thereof. Any of conventionally well known dyestuff acceptors can be mixed with the dyestuff acceptors of the present invention for their using.

Dyestuff acceptors are distributed and fixed on a carrier such as a paper by the above-mentioned processes. Marking of dense dark blue colour is formed in accordance with pressure on a support on which dyestuff acceptors are distributed by placing a paper distributed with dyestuff acceptors in such a way as the substance of the dyestuff acceptors being upside, piling a paper distributed with microcapsules containing CVL over the back surface thereof, and applying pressure thereon by a typewriter or writing means.

Dyestuff acceptors of the present invention have excellent color-forming ability for dyestuffs such as vanadium or iron compound system dyestuffs, too. However they are essentially different from dyestuff acceptors for the abovementioned proton sensitive dyestuffs in mechanism of formation of color, and therefore chemical structure of the dyestuff acceptors must be further restricted. Aromatic carboxylic acids, components of the dyestuff acceptors for vanadium or iron compound system dyestuffs, are represented by the general formula (V)

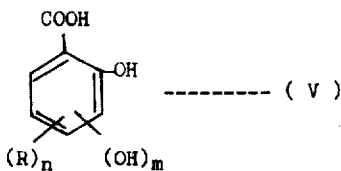

wherein $m$ is 1 or 2, $n$ is a positive integer of 1 to 3, and R represents a halogen, alkylgroup or aryl group and have at least 12 carbon atoms, which is included in formula (I). Concrete examples of compounds of general formula (V) are 3-hydroxy-5-($\alpha$, $\alpha$-dimethylbenzyl) salicylic acid, 3-hydroxy-4, 6-di($\alpha$, $\alpha$-dimethylbenzyl) salicylic acid, 3-hydroxy-5-cyclohexyl salicylic acid, 3-hydroxy-4, 6-dicyclohexylsalicylic acid, 3-hydroxy-4, 6-di-t-butylsalicylic acid, 4-hydroxy-5-cyclohexylsalicylic acid, 4-hydroxy-5($\alpha$, $\alpha$-dimethyl benzyl) salicylic acid, 4-hydroxy-5-t-octylsalicylic acid, 3, 5-di-t-butyl-6-hydroxysalicylic acid, 3, 5-dicyclohexyl-6-hydroxysalicylic acid, 3, 5-di ($\alpha$, $\alpha$-dimethylbenzyl)-6-hydroxysalicylic acid, 3, 6-di-t-butyl-5-hydroxy salicylic acid, 3-cyclohexyl-5-hydroxysalicylic acid, 4-cyclohexyl-5-hydroxy salicylic acid, 3, 6-dicyclohexyl-5-hydroxysalicylic acid, 4-($\alpha$, $\alpha$-dimethyl benzyl)-5-hydroxysalicylic acid, 3, 6-di($\alpha$, $\alpha$-dimethylbenzyl)-5-hydroxy salicylic acid, 4-t-octyl-5-hydroxysalicylic acid, 3, 4-dihydroxy-6-($\alpha$, $\alpha$-dimethylbenzyl) salicylic acid, 3, 4-dihydroxy-5-cyclohexyl salicylic acid, 3, 4-dihydroxy-5-t-octylsalicylic acid, 1-carboxy-2, 3-dihydroxy-6-($\alpha$, $\alpha$-dimethylbenzyl) naphthalene, 1-carboxy-2, 3-dihydroxy-7-($\alpha$, $\alpha$-dimethylbenzyl) naphthalene, 1-carboxy 2, 3-dihydroxy-6-t-butylnaphthalene, 1-carboxy-2, 3-dihydroxy-7-t-butyl naphthalene etc. All of these compounds as concrete examples can be produced by the same method as in case of said concrete examples. All of them form salts with polyvalent metals, but it is desirable to produce the salts by the abovementioned double decomposition. Moreover, it is desirable to select such polyvalent metals as the formed polyvalent metal salts of carboxylic acid being insoluble or hardly soluble in water. Further, many of compounds of general formula (V) are easily decarbonated at a high temperature under strong alkaline conditions. Therefore, double decomposition should be carried out under sufficient attentions.

Polyvalent metals which can be used for the object include aluminum, zinc, titanium, strontium, zirconium, tin, barium, antimony, lead and bismuth.

Thus prepared dyestuff acceptors can be distributed over the surface of papers by the same method as mentioned in detail in case of proton sensitive dyestuffs. It is a matter of course that stable and dense marking is obtained by matching these dyestuff acceptors with microcapsules containing vanadium or iron compounds as dyestuffs, but these dyestuff acceptors can be used by matching proton sensitive dyestuffs such as CVL. Since these dyestuff acceptors are distributed in form of fine powder on the surface of a paper, which is porous, and therefore a dyestuff solution is instantaneously absorbed to form color. This is an advantageous point of the present invention which has not been attained by conventional techniques.

Next, for making characteristic of the present invention clearer, the present invention is illustrated by showing concrete examples.

EXAMPLE 1

100 Grams of 3-phenylsalicylic acid, 30 grams of zinc oxide, 15 grams of polyvinyl alcohol and 800 ml. of water are placed in a porcelain ball mill with a capacity of 2000 ml., and milled with rotating for 24 hours. The composition is coated over a sheet of paper in an amount of 10~20 grams/m², and dried to form the support of a dyestuff acceptor. The support is positioned in such a way as the dyestuff acceptor coated face being upside and another sheet coated with micro capsules containing CVL is piled thereon in such a way as the microcapsules coated face contacting therewith. Then, pressure is applied thereon by a typewriter or writing means. Bright blue marking appears on the support of the dyestuff acceptor. The progress is effected at too short time to recognize by intuition and thus obtained marking is so stable that color is not faded away by influence of heat, light or water. Furthermore, the support of the dyestuff acceptors have colorforming ability not only for CVL, but also for other proton sensitive dyestuffs, and therefore these dyestuff acceptors are matched the support of microcapsules including a dyestuff solution containing one or more kinds of dyestuffs to attain markings of various color tones. Moreover, they are stable and bright as in CVL.

EXAMPLE 2

170 grams of orthophenylphenol are placed in a 500 ml. four-necked flask provided with a stirrer, a thermometer, a reflux condenser, and a dropping funnel. 0.5 g. of sulfuric acid is added therein and 236 g. of $\alpha$-methylstyrene is added gradually from the dropping funnel while stirring at 70°C. The dropping speed is high in the beginning and quite low at the end and it is controlled so as to complete dropping in 20 hours. Thus prepared products are substantially 2-{4'($\alpha$, $\alpha$-dimethylbenzyl) phenyl}-4-($\alpha$, $\alpha$-dimethylbenzyl) phenol. The whole amount of the products are dissolved in 400 g. of xylene and added further with 23 g. of dry metal sodium to dissolve. The solution is placed in an autoclave having a capacity of 1,000 ml. 20kg/cm² carbon dioxide gas pressure is blown thereinto, and reaction is carried out for about 3 hours. After cooling, gas pressure is removed and the contents are removed to another vessel. Then, 1,000 ml. of carbonated water is added and stirred. After standing still, the contents are separated into an oil layer and a water layer. 3 g. of active carbon is added to the water layer, well mixed and filtered off. When a sufficient amount of diluted sulfuric acid is added to the filtrate, white powder is prepared. The powder is filtered, washed with water and further recrystallized with xylene, to yield 270 g. of white crystals having a melting point of 185°C. Absorption of hydrogen bonded carbonyl group is observed at 1655 wave number in an infrared spectrum. The molecular weight measured by neutralization equivalent is 395 and substantially 3-{4'-($\alpha$, $\alpha$-dimethylbenzyl) phenyl} -5($\alpha$, $\alpha$-dimethylbenzyl) salicylic acid is contained.

EXAMPLE 2-1

One hundred grams of crystalline powder mainly composed of 3-{4'-($\alpha$, $\alpha$-dimethylbenzyl) phenyl}-5-($\alpha$, $\alpha$-dimethylbenzyl) salicylic acid prepared in Example 2, 10 g. of finely powdered aluminum hydroxide, 20 G. of rubber arabic, and 200ml of water are milled and mixed in a porcelain ball mill for 24 hours. 5 g. to 15 g. of the prepared composition are applied onto 1 m² of the surface of a sheet, and dried to form a support of a dyestuff acceptor.

EXAMPLE 2-2

Seventy grams of the products in Example 2 is dissolved in an aqueous caustic sodium solution, neutralized to make the total amount of 1000 ml. and 500 ml. of an aqueous solution containing aluminum sulfate of the same equivalent as the acid is added to form a precipitate. At that time, temperature of the liquor is adjusted not to raise above 45°C. 0.5 g. of formaldehyde condensates of naphthalene sulfonic acid sodium, synthetic rubber latex in an amount corresponding to 20 g of rubber components, 30 g of finely powdered silicic anhydride, and 50 g. of a 20% aqueous polyacrylamide solution are added, stirred strongly and mixed. 10~20 g. of the composition is applied over 1m² of the surface of a sheet and dried to form the support of a dyestuff acceptor.

EXAMPLE 3

Nine hundreds and forty grams of phenol is placed in a four-necked flask of 5000 ml. capacity, provided with a stirrer, a thermometer, a reflux condenser and a dropping funnel. 20 g. of sulfuric acid is added therein and 2360 g. of a $\alpha$-methylstyrene is added gradually with stirring at 50°C. The dropping speed and way are the same as in Example 2 and dropping is controlled so as to complete in 24 hours. After completion of dropping, the temperature is raised at 60°C, and aging is effected for about 5 hours. 1000 ml. of a 1% aqueous sodium carbonate solution is added and the temperature is raised up to 90°C. with stirring. The solution is stood still until it is separated into two layers. The upper water layer is taken out and washed further with 1000 ml. of water, twice. The oil layer is dehydrated and distilled at about 1mmHg. About 2700 g. of main distillates are gathered by distilling at about 200°C. The distillates contain 98% of 2, 4-di($\alpha$, $\alpha$-dimethylbenzyl) phenol. 2500 g. of 2, 4-di($\alpha$, $\alpha$-dimethylbenzyl) phenol is placed in a 5000 ml flask and added further with 2000 ml of xylene. Water is removed azeotropically, while dropping a concentrated aqueous solution containing the same equivalent as said phenol, of caustic sodium with heating at a boiling temperature. Thereby, anhydrides of sodium salts of said phenol are obtained. The anhydrides are placed in an autoclave having a capacity of 1000 ml and carbon dioxide gas of pressure of 30kg/cm² is blown into at 160°C., to react for about 5 hours. After cooling, gas pressure is removed and the contents are removed to another vessel and added with 1500 ml. of water, followed by stirring. At that time, unless the temperature of the solution is maintained at a temperature above about 70°C., the products become fine crystals and the solution becomes gel. After separating the oil layer by standing still, diluted sulfuric acid is added to yield fine crystals of 3, 5-di($\alpha$, $\alpha$-dimethylbenzyl) salicylic acid. When they are recrystallized with xylene, about 2000 g. of pure crystals (melting point 187°C.) are obtained. It was confirmed by an infrared spectrum and neutralization equivalent that the crystals are 3, 5-di($\alpha$, $\alpha$-dimethylbenzyl) salicylic acid.

EXAMPLE 3-1

Three hundreds and thirty grams (1mol) of 3, 5-di($\alpha$, $\alpha$-dimethylbenzyl) salicylic acid prepared in Example 3 is dissolved in 2000 ml. of an aqueous solution containing equivalent amount of caustic sodium by heating. Separately, 3000 ml. of an aqueous solution containing 1, 2 equivalent zinc sulfate is placed in a vessel having a capacity of 10000 ml. and the above-mentioned solution is added gradually with strong stirring. Precipitates are formed. Therefore, the precipitates are filtered and washed sufficiently with water. The precipitates are in a water-containing condition and are obtained as cake containing about 25% solid content. Into 1000 g of the cake, 1, 5 g of formaldehyde condensates of naphthalene sulfonic acid sodium, 150 g of an aqueous solution containing 20% copolymer of 70% acrylamide and 30% methylol acryl amide, and 200 g of latex of styrene butadine polymer with 30% concentration are added. About 500 g. of water is added with stirring to adjust consistency. About 10 g of 20% diluted sulfuric acid is added immediately before application and mixed well. 5~20g of the composition is applied to 1m² of the surface of a sheet and dried to form the support of a dyestuff acceptor.

EXAMPLE 3-2

Three hundreds and thirty grams of 3, 5-di($\alpha$, $\alpha$-dimethylbenzyl) salicylic acid obtained in Example 3 is dissolved into an aqueous solution containing the equivalent of caustic sodium at an elevated temperature. Separately, an aqueous solution containing 1,2 equivalent of aluminum sulfate is placed into a vessel having a capacity of 10000ml., and the above-mentioned aqueous solution is gradually added therein with strongly stirring. Precipitates are formed and subjected to filtration and washing with water. The precipitates are 3, 5-di($\alpha$, $\alpha$-dimethylbenzyl) salicylic acid aluminum and obtained in form of about 20% cake. An aqueous solution containing 50 g, of finely powdered silicic anhydride and 70 g, of polyvinyl alcohol, 5 g of glyoxal and water are added therein and stirred sufficiently to make the total amount 3000 ml. 5~20 g of the composition is applied onto 1m² of the surface of a sheet, and dried to form the support of a dyestuff acceptor.

EXAMPLE 4

Two hundreds and ninety four grams of 2-cyclohexyl-4-($\alpha$, $\alpha$-dimethylbenzyl) phenol is dissolved in 500 g of xylene and further added with 23 g of dried metal sodium. The solution is removed to an autoclave having a capacity of 1000 ml. of carbon dioxide gases are blown therein at a temperature of 140°C. under gas pressure up to 20kg/cm² to effect a reaction for about 5 hours, followed by cooling. By same treatments as in Examples 2 and 3, about 180 g. of fine crystals of 3-cyclohexyl-5-($\alpha$, $\alpha$-dimethylbenzyl) salicylic acid (melting point, 137°C) are obtained.

EXAMPLE 4-1

Fifty grams of 3-cyclohexyl-5-($\alpha$, $\alpha$-dimethylbenzyl) salicylic acid obtained in Example 4 is dissolved in 500 ml. of an aqueous caustic sodium solution at an elevated temperature, to make the solution neutral. An aqueous solution containing the same equivalent as the acid, of aluminum sulfate is added to form precipitates. The precipitates are filtered, washed and again dispersed in water containing 15 g. of polyvinyl alcohol and 3 g. of glyoxal to make the total amount 500ml. 5g~10g. of the composition is applied uniformly onto 1m$^2$ of the surface of a sheet and dried by heating, thereby to form the support of a dyestuff acceptor.

EXAMPLE 4-2

Fifty grams of 3-cyclohexyl-5-($\alpha$, $\alpha$-dimethylbenzyl) salicylic acid obtained in Example 4 is dissolved in 500ml. of an aqueous caustic sodium solution by heating, to make the solution neutral. 500 ml. of an aqueous solution containing the same equivalent as the acid, of zinc sulfate is added therein to separate precipitates. The precipitates are well stirred, added with an aqueous solution containing 1g. of manganese sulfate and further stirred well. Then, the precipitates are filtered and washed. The precipitates are redispersed in an aqueous solution containing 15 g. of rubber arabic to make the total amount 500 ml. 5~20 g. of the composition is applied onto 1m$^2$ of the surface of a sheet and dried to form the support of a dyestuff acceptor.

EXAMPLE 5

3-($\alpha$, $\alpha$-dimethylbenzyl)-5-cyclohexyl salicylic acid is produced by the quite same methods as in Examples 2 and 4 from 2-($\alpha$, $\alpha$-dimethylbenzyl)-4-cyclohexyl phenol.

EXAMPLE 5-1

Fifty grams of 3-($\alpha$, $\alpha$-dimethylbenzyl)-5-cyclohexyl salicylic acid obtained in Example 5 is disolved in 500ml. of an aqueous caustic sodium solution, to make the solution neutral. 300 g. of an aqueous solution containing the same equivalent as the acid, of manganese sulfate is added therein to separate precipitates. The precipitates are filtered and washed with water and added further with a solution containing 15 g. of polyvinyl alcohol, to make the total amount 500 ml. 5~20 g. of the composition is applied onto 1m$^2$ of the surface of a sheet and dried to form the support of a dyestuff acceptor.

EXAMPLE 5-2

Fifty grams of 3-($\alpha$, $\alpha$-dimethylbenzyl)-5-cyclohexyl-salicylic acid obtained in Example 5 is dissolved in 500 ml. of an aqueous caustic sodium solution, to make the solution neutral. 500 ml. of an aqueous solution containing the same equivalent as the acid, of zinc sulfate is added therein, to separate precipitates. The precipitates are filtered, washed with water, added with an aqueous solution containing 15 g. of methyl cellulose, to make the total amount 700 ml. 5~20 g. of the composition is applied onto 1m$^2$ of the surface of a sheet and dried to form the support of a dyestuff acceptor.

EXAMPLE 6

Two hundreds and twenty eight grams (1 mol) of bisphenol A is placed in a 500 ml. four-necked flask provided with a stirrer, a thermometer, a reflux condenser and a dropping funnel and added with 4 g. of paratoluene sulfonic acid at an elevated temperature up to 165°C. 260 g. (2, 2 mols) of $\alpha$-methyl styrene is gradually dropped from the dropping funnel by operating the stirrer. With progress of dropping, the temperature is lowered until it is 90°C. at the time when the half of $\alpha$-methylstyrene was dropped. Dropping is controlled by adjusting the dropping speed, so as to complete the dropping in about 15 hours. From the results of analysis of a gas chromatography of the reaction product, it is presumed that the composition is one containing substantially a mixture of 2-($\alpha$, $\alpha$-dimethylbenzyl)-4-($\alpha'$, $\alpha'$-dimethyl-4-hydroxybenzyl)phenol, 2-($\alpha$, $\alpha$-dimethylbenzyl)-4-{$\alpha'$, $\alpha'$-dimethyl-3'-($\alpha''$, $\alpha''$-dimethylbenzyl)-4'-hydroxybenzyl} phenol and 2-($\alpha$, $\alpha$-dimethylbenzyl)-4-{$\alpha'$, $\alpha'$-dimethyl-3', 5'-di($\alpha''$, $\alpha''$-dimethylbenzyl)-4'-hydroxybenzyl} phenol. The composition is dissolved in 400 ml. of xylene, and further added with 30 g. of dried metal sodium and dissolved. The solution is placed in an autoclave having a capacity of 1000ml. and carbon dioxide gas of pressure of 20kg/cm$^2$ is blown therein at 150°C. to effect a reaction for about 5 hours. By treating the products in the same manner as in Examples 2 and 4, a mixture of nucleus-substituted salicylic acids is obtained. Absorption of a strongly hydrogen-bonded carbonyl group is observed at a band near 1660 wave number of an infrared spectrum, and formation of nucleus-substituted salicylic acid is confirmed.

EXAMPLE 6-1

Fifty grams of the product obtained in Example 6 is dissolved in 500 ml. of caustic sodium to make a solution neutral. With adding 500 ml. of an aqueous solution of 1.2 equivalents, to the required caustic sodium, of zinc sulfate, strong stirring is carried out. The formed precipitates are filtered and washed. An aqueous solution containing 10 g. of polyacryl amide, latex of styrene-butadiene copolymer containing 20g. of rubber components and water are added therein, to make the total amount 500ml, followed by well stirring. About 5~20g. of the composition is applied onto 1m$^2$ of the surface of a sheet and dried to form the support of a dyestuff acceptor.

EXAMPLE 7

One hundred and sixty four grams of 2-tertiarybutyl-4-methylphenol is dissolved in 500ml. of xylene. 23g. of dried metal sodium is added therein and dissolved. The resulting product is a suspension of white powder in xylene. The product is placed in a porcelain ball mill having a capacity of 1000 ml., and milled for about 3 hours. The product is placed in an autoclave having a capacity of 1000 ml. and carbon dioxide gas pressure of 20kg/cm$^2$ is blown therein at about 150°C. to effect a reaction for about 5 hours. By same treatments thereof as in Examples 2 and 4, 3-tertiary butyl-5-methylsalicylic acid is produced.

EXAMPLE 7-1

A composition containing 3-tertiarybutyl-5-methyl-salicylic acid zinc and polyvinyl alcohol is applied to the surface of a sheet and dried in the same manner as in each Example, to form the support of a dyestuff acceptor.

EXAMPLE 8

3, 5-ditertiary butyl salicylic acid is produced from 2, 4-ditertiary butylphenol in the same manner as in Example 6.

EXAMPLE 8-1

Five kilograms of 3, 5-ditertiary butylsalicylic acid prepared in Example 8 is dissolved in 50 l. of an aqueous caustic sodium solution to make the solution neutral. The abovementioned aqueous solution is added to a pulp suspension containing 100 kg. of pulp and 50 l. of an aqueous solution containing 1.2 times of equivalent, to acid, of aluminum sulfate is gradually added to the pulp suspension with stirring. Then, a small amount of an aqueous caustic sodium solution is added until the solution does not show alkaline property. By such means, aluminum salts of 3, 5-ditertiary butyl salicylic acid are deposited on the pulp fibers. Papers are made from the pulp suspension, the paper substance of which contains uniformly distributed dyestuff acceptors.

EXAMPLE 9

Two hundreds and twelve grams of 4-($\alpha$, $\alpha$-dimethylbenzyl) phenol is dissolved in 700 ml. of xylene, and water is azeotropically removed with dropping an aqueous solution containing 40 g. of caustic sodium, while the solution is strongly stirred. Sodium salts of 4-($\alpha$, $\alpha$-dimethylbenzyl) phenol are powdery and suspended with xylene. The suspension is transferred to an autoclave having a capacity of 1000ml. and 20kg/cm$^2$ of carbondioxide gas pressure is blown therein at 150°C., thereby to react for about 5 hours. After cooling, about 130g. of 5-($\alpha$, $\alpha$-dimethylbenzyl) salicylic acid (melting point, 159°C.) is obtained by the same way as in Example 2. A composition containing 5-($\alpha$, $\alpha$-dimethylbenzyl) salicylic acid zinc and acrylamide-methylol acrylamide copolymer is applied to the surface of a sheet and dried to yield the support of a dyestuff acceptor.

EXAMPLE 10

Two hundreds and sixteen grams of paracresol is placed in a 500 ml. four-necked flask equipped with a stirrer, a thermometer, a reflux condenser and a dropping funnel. 4g. of sulfuric acid is added therein and 236 g. of $\alpha$-methyl styrene is dropped gradually at 60°C. with stirring. The dropping speed is adjusted to complete dropping in about 20 hours. Thus, 2-($\alpha$, $\alpha$-dimethylbenzyl)-4-methylphenol is obtained. The resulting material is dissolved in 500 ml. of xylene and water is azeotropically removed with dropping an aqueous solution containing 80g. of caustic sodium. The solution is transferred to an autoclave having a capacity of 1000ml., and treated by the same way as in Example 9, to yield about 300g. of 3-($\alpha$, $\alpha$-dimethylbenzyl)-5-methylsalicylic acid. By same treatments as in each Example, 900ml. of a composition containing 100g. of 3-($\alpha$, $\alpha$-dimethylbenzyl)-5-methylsalicylic acid zinc, 20g. of styrene-butadiene copolymer, 15g. of acrylamide-methylol acrylamide copolymer, 0.3g. of a sulfonic acid salt type surface active agent and water is prepared. About 5~15g. of the composition is applied to 1m$^2$ of the surface of a sheet and dried to form the support of a dyestuff acceptor.

EXAMPLE 11

A mixture of 6-($\alpha$, $\alpha$-dimethylbenzyl)-2-hydroxy-1-naphthoic acid and 6-($\alpha$, $\alpha$-dimethylbenzyl)-2-hydroxy-3-naphthoic acid is prepared from 6-($\alpha$, $\alpha$-dimethylbenzyl)-2-naphthole by the same method as in Example 9. 50g. of the mixture is dissolved in 500ml. of an aqueous caustic sodium solution to make the solution neutral. 500ml. of an aqueous solution containing the same equivalent as the acid, of zinc sulfate is added to form precipitates. The precipitates are filtered, washed with water and added with an aqueous solution containing 20g. of methylcellulose to make the total amoutn 500ml. 10~20 g. of the composition is applied onto 1m$^2$ of the surface of a sheet and dried to form the support of a dyestuff acceptor.

EXAMPLE 12

Fifty grams of 3-phenyl salicylic acid is dissolved in 500ml. of an aqueous caustic sodium solution to make the solution neutral. 500ml. of an aqueous solution containing the same equivalent as the acid, of zinc sulfate is added to form precipitates. 1000ml. of toluene and 1g. of a non-ionic surface active agent prepared by adding 6 moles of ethylene oxide into styrenated phenol are added and sufficiently stirred. Precipitates of zinc salts of 3-phenylsalicylic acid migrate to a toluene layer. A water layer is separated and the toluene layer is distilled and concentrated under a reduced pressure to make the total amount 400ml. of 20g. of petroleum resin (mainly formaldehyde condensates of metaxylene) is added therein and well mixed. The composition is suitable for printing by photogravure-printing system. 5~20g. of the composition is printed onto 1m$^2$ of the surface of a sheet and dried to form the support of a dyestuff acceptor.

EXAMPLE 13

Fifty grams of 3-{4'-($\alpha$, $\alpha$-dimethylbenzyl) phenyl}-5-($\alpha$, $\alpha$-dimethyl benzyl) salicylic acid is dissolved in 500ml. of an aqueous caustic sodium solution, to make the solution neutral. 500ml. of an aqueous solution containing ¼ equivalents to acid of calcium chloride and ¼ equivalents of aluminum chloride is added to form precipitates. The precipitates are well filtered, washed with water and dispersed in an aqueous solution containing 15g. of trimethylol melamine and 0.2g. of alkyl benzene sulfonic acid sodium, to make the total amount 400ml. 5~20g. of the composition is applied to 1m$^2$ of the surface of a sheet and dried to form the support of a dyestuff acceptor.

EXAMPLE 14

Fifty grams of 3-{4'-($\alpha$, $\alpha$-dimethylbenzyl) phenyl}-5-($\alpha$, $\alpha$-dimethyl benzyl) salicylic acid is dissolved in 400ml. of an aqueous caustic sodium solution to make the solution neutral. 15g. of an aqueous solution containing acrylic acid sodium with a low viscosity and 15g. of silicic anhydride in form of fine powder are added to make the total amount 600ml. The mixture is strongly stirred. 10~20g. of the composition is applied onto 1m$^2$ of the surface of a sheet. Successively, 5~10g. of a 10% aqueous solution of zinc sulfate is applied thereon and dried to form the support of a dyestuff acceptor.

EXAMPLE 15

The support of a dyestuff acceptor containing 3, 5-ditertiary butyl salicylic acid zinc is prepared by the same way as in each of the above mentioned Examples.

EXAMPLE 16

The support of a dyestuff acceptor containing 3-tertiary octyl-5-methyl-salicylic acid zinc is prepared by the same way as in each of the above-mentioned Examples.

EXAMPLE 17

The support of a dyestuff acceptor containing 3-($\alpha$, $\alpha$-dimethylbenzyl)-5-methylsalicylic acid aluminum is prepared by the same way as in each of the above-mentioned Examples.

EXAMPLE 18

The support of a dyestuff acceptor containing 3-($\alpha$, $\alpha$-dimethylbenzyl)-5-cyclohexyl salicylic acid aluminum is prepared by the same way as in each of the above-mentioned Examples.

EXAMPLE 19

3, 5-dicyclohexyl salicylic acid is produced from a mixture of 2, 4-dicyclohexyl phenol and 2, 6-dicyclohexyl phenol (mixture ratio of about 3:1), using an amount equivalent to 2, 4-dicyclohexyl phenol of caustic sodium and carbon dioxide gases by the same way as in each Example. The support of a dyestuff acceptor containing 3, 5-dicyclohexyl salicylic acid zinc is prepared therefrom by the same treatments as in each Example.

EXAMPLE 20

The support of a dyestuff acceptor containing 3, 5-di($\alpha$, $\alpha$-dimethylbenzyl)-6-methyl salicylic acid aluminum is prepared by the same method as in each Example.

EXAMPLE 21

The support of a dyestuff acceptor containing a mixture of zinc salts of 5-($\alpha$, $\alpha$-dimethyl-4'-hydroxybenzyl) salicylic acid, 5-($\alpha$, $\alpha$-dimethyl-3'-tertiary butyl-4'-hydroxybenzyl) salicylic acid, 5-($\alpha$, $\alpha$-dimethyl-3'-carboxy-4'-hydroxybenzyl) salicylic acid, 3-tertiarybutyl-5-($\alpha$, $\alpha$-dimethyl-3'-tertiary butyl-4'-hydroxybenzyl) salicylic acid and 3-tertiarybutyl-5-($\alpha$, $\alpha$-dimethyl benzyl-3', 5'-ditertiary butyl-4'-hydroxybenzyl) salicylic acid is prepared by the same method as in each Example.

When a recording paper having the support of a dyestuff acceptor obtained in Examples 2~21 is matched with a proton sensitive dyestuff as in Example 1, marking by pressure is quite stable and dense and does not disappear easily by heat, light or water, and moreover density is not reduced thereby. Further, effects as a dyestuff acceptor can be lost by giving function of a desensitizer as in conventional dyestuff acceptors.

EXAMPLE 22

Fifty grams of 3-hydroxy-5-($\alpha$, $\alpha$-dimethylbenzyl) salicylic acid is dissolved in 300ml. of an aqueous caustic sodium solution, to make the solution neutral. 200ml. of an aqueous solution containing the same equivalent, as the acid, of zinc sulfate is added thereto, to form precipitates. The precipitates are washed with water, filtered and redispersed in an aqueous solution containing 15g. of methyl cellulose to make the total amount 500ml. 5~20g. of the composition is applied to 1m² of the surface of a sheet and dried to form the support of a dyestuff acceptor.

EXAMPLE 23

Fifty grams of a mixture of 1-carboxy-2, 3-dihydroxy-6-($\alpha$, $\alpha$-dimethyl benzyl) naphthalene and 1-carboxy-2, 3-dihydroxy-7-($\alpha$, $\alpha$-dimethylbenzyl) naphthalene is dissolved in 500ml. of an aqueous caustic sodium solution to make the solution neutral. 500ml. of an aqueous solution containing the same equivalent as the acid, of aluminum sulfate is added therein to form precipitates. The precipitates are filtered, washed with water, and dispersed in an aqueous solution containing 15g. of acrylamide-methylolacrylamide copolymer, to make the total amount 400ml. 10~20g. of the composition is applied to 1m² of the surface of a sheet and dried to form the support of a dyestuff acceptor.

EXAMPLE 24

The support of a dyestuff acceptor containing 3, 5-di($\alpha$, $\alpha$-dimethylbenzyl)-6-hydroxysalicylic acid aluminum is prepared by the same methods as in said Examples 22 and 23.

When the support of a dyestuff acceptor prepared in said Examples 22~24 is matched with a proton sensitive dyestuff, stable and dense marking is obtained as in Examples 1~21. When it is matched with a dyestuff of vanadium or iron compound type, a complex is formed and stable marking is obtained. Vanadium or iron compounds in oil-soluble or water-soluble conditions are included in microcapsules.

Moreover, as in the abovementioned Examples, the dyestuff acceptor of the present invention causes formation of stable and dense color with a dyestuff, and the minimum amount of the dyestuff acceptor or dyestuff is sufficiently used in comparison with conventional dyestuff acceptors. It is one of great advantages because the weight or thickness of a recording paper is made minimum.

We claim:

1. Pressure sensitive recording paper which comprises a two-component system in which one component is paper coated with a color developer composition and the other component is a recording paper having an encapsulated dyestuff layer, said dyestuff consisting essentially of a proton sensitive dyestuff of the crystal violet lactone type, and said developer composition contains a salicylic acid derivative selected from the group consisting of: aluminum 3-phenyl-5-($\alpha$, $\alpha$-dimethyl-benzyl) salicylate, zinc 3-phenyl-5-($\alpha$, $\alpha$-dimethyl-benzyl), salicylate, zinc 3-tert-butyl-5 methylsalicylate, zinc 3-phenylsalicylate, zinc 3-cyclohexylsalicylate, zinc 3-($\alpha$, $\alpha$-dimethylbenzyl)-5-methylsalicylate, zinc 3, 5-di-tert-butylsalicylate zinc 3, 5-dicyclohexyl-salicylate, zinc 3-cyclohexyl-5-($\alpha$, $\alpha$-dimethylbenzyl) salicylate, zinc 3,5-di ($\alpha$-methylbenzyl) salicylate, zinc 3-($\alpha$-methylbenzyl)-5-($\alpha$, $\alpha$-dimethylbenzyl) salicylate, zinc 3,5-di($\alpha$, $\alpha$-dimethylbenzyl) salicylate, a mixture of zinc 3-cyclohexyl-5-($\alpha$, $\alpha$-dimethylbenzyl) salicylate and zinc 3,5-di ($\alpha$, $\alpha$-dimethylbenzyl) salicylate.

2. Pressure sensitive recording paper according to claim 1, wherein said paper is made from a pulp produced by effecting double decomposition of an alkali metal salt or ammonium salt of salicylic acid derivatives as defined in claim 65 and a water-soluble polyvalent metal salt in a pulp suspension and depositing the polyvalent metal salt of salicylic acid derivatives on the pulp fibres.

3. Pressure sensitive recording paper according to claim 1, wherein said developer composition contains at least one member selected from the group consisting of silicic acid, boric acid, carbonic acid, and polyvalent metal oxides, said member acting as an auxiliary.

* * * * *